United States Patent [19]

Saji et al.

[11] Patent Number: 5,081,139

[45] Date of Patent: Jan. 14, 1992

[54] N-SUBSTITUTED TRIAZOLE DERIVATIVES AND FUNGICIDAL USE THEREOF

[75] Inventors: Ikutaro Saji; Yoshihiro Tanaka, both of Osaka; Katsuaki Ichise; Tomoharu Tanio, both of Kyoto; Takao Okuda, Osaka; Toshio Atsumi, Kawanishi, all of Japan

[73] Assignee: Sumitomo Pharmaceuticals Company, Limited, Osaka, Japan

[21] Appl. No.: 783,185

[22] Filed: Oct. 2, 1985

[30] Foreign Application Priority Data

Oct. 2, 1984 [JP] Japan .................. 59-207634
Dec. 17, 1984 [JP] Japan .................. 59-265982

[51] Int. Cl.$^5$ .................... A61K 31/41; C07D 249/08
[52] U.S. Cl. .................... 514/383; 548/268.6
[58] Field of Search .................... 548/262, 268.6; 514/383

[56] References Cited

U.S. PATENT DOCUMENTS 4,496,388  1/1985  Clough .................... 548/101

FOREIGN PATENT DOCUMENTS 0054974  6/1982  European Pat. Off. .
0078594  5/1983  European Pat. Off. .
0091398  10/1983 European Pat. Off. .
0095828  11/1983 European Pat. Off. ............ 548/262
0107392  5/1984  European Pat. Off. .
0113644  7/1984  European Pat. Off. .
2103210  6/1982  United Kingdom ................ 548/262

*Primary Examiner*—Patricia L. Morris
*Attorney, Agent, or Firm*—Birch, Stewart, Kolasch & Birch

[57] ABSTRACT

An N-substituted triazole compound of the formula:

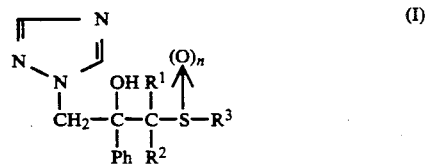

wherein Ph is a phenyl group or a phenyl group substituted with one or two halogen atoms, $R^1$ is a $C_1$–$C_3$ alkyl group, $R^2$ is a hydrogen atom or a $C_1$–$C_3$ alkyl group, $R^3$ is a $C_1$–$C_8$ alkyl group, a $C_4$–$C_8$ cycloalkylalkyl group or a $C_3$–$C_6$ cycloalkyl group and n is 0, 1 or 2, or an acid addition salt thereof, which is useful as an antifungal agent.

49 Claims, No Drawings

N-SUBSTITUTED TRIAZOLE DERIVATIVES AND FUNGICIDAL USE THEREOF

The present invention relates to N-substituted triazole derivatives, and their production and use.

More particularly, it relates to N-substituted triazole derivatives of the formula:

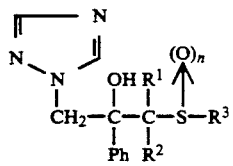

wherein Ph is a phenyl group or a phenyl group substituted with one or two halogen atoms, $R^1$ is a $C_1$-$C_3$ alkyl group, $R^2$ is a hydrogen atom or a $C_1$-$C_3$ alkyl group, $R^3$ is a $C_1$-$C_8$ alkyl group, a $C_4$-$C_8$ cycloalkylalkyl group or a $C_3$-$C_6$ cycloalkyl group and n is 0, 1 or 2, and their acid addition salts, and their preparation process and their antifungal use.

In the above significances, the term "halogen" covers fluorine, chlorine, bromine and iodine. The term "$C_1$-$C_3$ alkyl" covers methyl, ethyl, n-propyl and isopropyl The term "$C_1$-$C_8$ alkyl" is intended to mean a straight or branched alkyl group having 1 to 8 carbon atoms (e.g. methyl, ethyl, n-propyl, isopropyl, n-butyl, sec-butyl, isobutyl, t-butyl, n-pentyl, isopentyl, t-pentyl, n-hexyl, n-heptyl, n-octyl). The term "$C_4$-$C_8$ cycloalkylalkyl" may be cyclopropylmethyl, cyclobutylethyl, cyclopentylmethyl, cyclohexylmethyl, etc. The term "$C_3$-$C_6$ cycloalkyl" may be cyclopropyl, cyclobutyl, cyclopentyl, cyclohexyl, etc.

Among various compounds represented by the formula (I), those wherein Ph is a phenyl group substituted with halogen, $R^1$ is a methyl group, $R^2$ is a hydrogen atom or a methyl group, $R^3$ is a methyl group and n is 1 or 2 are preferred. Particularly preferred are those wherein Ph is a 2,4-dichlorophenyl group or a 2,4-difluorophenyl group, $R^1$ and $R^3$ are each a methyl group, $R^2$ is a hydrogen atom and n is 2.

The N-substituted triazole derivatives (I) of the invention may be prepared in either an optically active form or a racemic form. For instance, in case of a diastereomer, it can be isolated by a per se conventional separation procedure such as chromatography. Each diastereomer may further be resolved into optical isomers by a per se conventional procedure. Thus, the scope of the invention is not limited to the racemic form but encompasses the individual optical isomers.

The N-substituted triazole derivatives are novel and useful as pharmaceuticals, particularly for controlling fungal infections such as mycosis in mammals including human beings.

Japanese Patent Publication (unexamined) No. 15964/83 discloses that certain sulfides having a 1,2,4-triazole group are useful for controlling plant pathogenic fungi. However, the N-substituted triazole derivative (I) according to the invention are not disclosed therein As the result of an extensive study, it has now been found that the N-substituted triazole derivatives (I) exhibit a prominent antifungal activity, particularly in continuous administration, while exerting less toxicity to mammals. This invention is based on this finding.

For preparation of the N-substituted triazole derivatives (I), there may be adopted various procedures, among which typical ones are as follows:

Procedure A

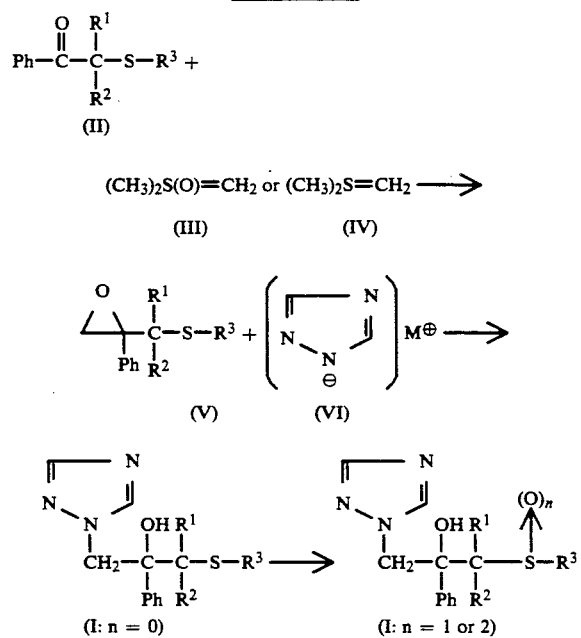

wherein M is an alkali metal atom (e.g. sodium, potassium, lithium) and $R^1$, $R^2$ and $R^3$ are each as defined above.

Namely, the ketone compound (II) (U.S. Pat. No. 4,128,581) is first reacted with dimethyloxosulfonium methylide (III) or dimethylsulfonium methylide (IV), and the resultant epoxide compound (V) is then reacted with an alkali metal salt of 1,2,4-triazole to give the sulfide compound (I: n=0), which is oxidized to the sulfinyl or sulfonyl compound (I: n=1 or 2).

The reaction between the ketone compound (II) and dimethyloxosulfonium methylide (III) or dimethylsulfonium methylide (IV) may be effected in an inert solvent (e.g. dimethylsulfoxide, acetonitrile) at a temperature of from 0 to 60° C. The amount of the dimethyloxosulfonium methylide (III) or dimethylsulfonium methylide (IV) is usually from 1 to 5 equivalents, preferably from 1 to 2 equivalents, to the ketone compound (II).

The subsequent reaction of the epoxide compound (V) with the alkali metal salt of 1,2,4-triazole (VI) is usually carried out in an inert solvent (e.g. dimethylformamide, dimethylacetamide) at a temperature of from room temperature to the boiling point of the solvent, preferably of from 70 to 120° C. The amount of the alkali metal salt of 1,2,4-triazole (VI) is usually from 1 to 5 equivalents, preferably from 1 to 3 equivalents, to the epoxide compound (V).

The oxidation of the sulfide compound (I: n=0) may be carried out by treatment with an oxidizing agent such as a peracid (e.g. m-chloroperbenzoic acid) in an inert solvent such as a halogenated hydrocarbon (e.g. chloroform) at a temperature of from −30° C. to the boiling temperature of the solvent, preferably of from 0° C. to room temperature. The amount of the oxidizing agent used for obtaining the sulfinyl compound (I: n=1) is usually about an equivalent to the sulfide compound (I: n=0). The amount of the oxidizing agent used for the synthesis of the sulfonyl compound (I: n=2) is usually more than 2 equivalents to the sulfide compound (I: n=0), preferably from 2 to 3 equivalents to the sulfide compound (I: n=0).

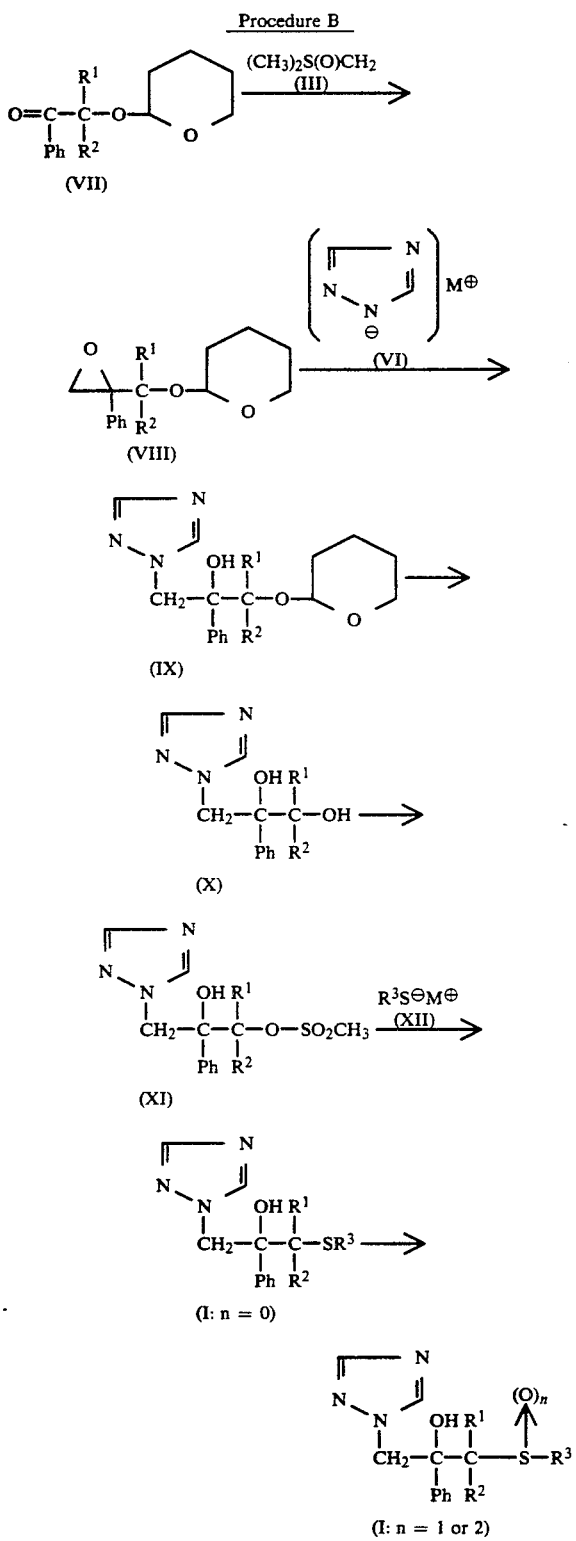

wherein Ph, $R^1$, $R^2$ and $R^3$ are each as defined above.

Namely, the ketone compound (VII) (Chem.Ber., 116, 3631 (1983); J.Gen.Chem., 22, 1197 (1952); J.Chem.Soc., 3649 (1950)) is first reacted with dimethyloxosulfonium methylide (III) in an inert solvent (e.g. dimethylsulfoxide) at a temperature of from 0 to 60° C. to give the epoxide (VIII). The amount of the dimethyloxosulfonium methylide (III) is usually from 1 to 5 equivalents, preferably from 1 to 2 equivalents, to the ketone compound (VII). The epoxide (VIII) is then reacted with an alkali metal salt of 1,2,4-triazole (VI) in an inert solvent (e.g. dimethylformamide) to give the triazolyl alcohol (IX). The amount of the alkali metal salt (e.g. sodium, potassium, lithium) of 1,2,4-triazole (VI) is usually from 1 to 5 equivalents, preferably from 1 to 3 equivalents, to the epoxide (VIII). The reaction temperature is normally from room temperature to the boiling point of the solvent, preferably from 70 to 20° C.

The triazolyl alcohol (IX) is then hydrolyzed with an acid in an aqueous medium to give the diol (X). As the acid, there may be used, for instance, hydrochloric acid, sulfuric acid, etc. The amount of the acid may be from 1 to 5 equivalents to the triazolyl alcohol (IX). The reaction temperature is normally from 0 to 80° C., preferably from 0 to 30° C.

The diol (X) is then reacted with methanesulfonyl chloride in the presence of a base in an inert solvent (e.g. benzene, chloroform, dichloromethane) at a temperature of from 0 to 30° C. to give the mesylate (XI). The amount of the methanesulfonyl chloride may be from 1 to 2 equivalents to the diol (X). As the base, there may be used, for instance, pyridine, triethylamine, etc. The amount of the base may be from 1 to 5 equivalents to the diol (X).

The mesylate (XI) is then reacted with an alkali metal salt of a thiol (XII) in an inert solvent (e.g. dimethylsulfoxide, dimethylformamide, water) at a temperature of from 0 to 80° C., preferably from 50 to 60° C., to give the sulfide (I: n=0). The amount of the alkali metal salt (e.g. sodium, potassium, lithium) of the thiol (XII) may be from 2 to 10 equivalents to the mesylate (XI).

The sulfide (I: n=0) can be oxidized to the sulfoxide or sulfone (I: n=1 or 2) in the same manner as described in Procedure A.

The acid addition salts of the N-substituted triazole derivatives (I) may be prepared by treatment of the N-substituted triazole derivative (I) with an acid in a per se conventinal procedure for salt formation. Examples of the acid are inorganic acids (e.g. hydrochloric acid, hydrobromic acid, phosphoric acid, nitric acid, sulfuric acid) and organic acids (e.g. oxalic acid, acetic acid, maleic acid, succinic acid, fumaric acid, tartaric acid, citric acid, salicylic acid, sorbic acid, lactic acid). The acid addition salts are preferred to be physiologically acceptable.

The N-substituted triazole derivatives (I) exhibit a strong antifungal activity against various fungi. The in vivo test of the antifungal activity with some representatives of the N-substituted triazole derivatives (I) was carried out in the following manner:

Candida albicans KB-8 as pre-cultured at 30° C. for 4 days was suspended in physiologically saline solution, and the suspension was intravenously injected into DDY strain male mice of 5 weeks old, every 10 animals being grouped, through the tail vein so as to inoculate a cell number of $10^7$ per animal. The animals were orally medicated with the test compound in the form of 0.5 % methylcellulose suspension at a total dose of 1 mg or 20 mg per kg of the body weight 0, 5, 24 and 48 hours after the infection, and observation was continued for 10 days after the infection.

The results are shown in Table 1, wherein the survival rate at complete death of non-medicated group (control) and the average number of survival days of 10 animals as one group in contrast to that of the non-medicated (control) group were indicated.

TABLE 1

Antifungal activity in vivo $$\begin{array}{c} \text{N} \\ \parallel \\ \text{N} \\ \mid \\ \text{N} \\ \mid \\ \text{CH}_2-\overset{\text{OH}}{\underset{\mid}{\text{C}}}-\overset{R^1}{\underset{\mid}{\text{C}}}-\overset{(O)_n}{\underset{\mid}{\text{S}}}-R^3 \\ \overset{\mid}{\text{Ph}} \quad \overset{\mid}{R^2} \end{array} \quad (I)$$

| Compound No. | Ph | $R^1$ | $R^2$ | $R^3$ | n | Dose (mg/kg) (p.o.) | Survival rate at complete death of non-medicated group (%) | Average survival days(s) |
|---|---|---|---|---|---|---|---|---|
| 1A | 2,4-Dichlorophenyl | Methyl | H | n-Propyl | 0 | 20 | 100 | 10.0 |
| 2Aa | 2,4-Dichlorophenyl | " | " | " | 1 | 1 | 70 | 6.2 |
|  |  |  |  |  |  | 20 | 100 | 10.0 |
| 2Ab | 2,4-Dichlorophenyl | " | " | " | 1 | 20 | 100 | 10.0 |
| 3A | 2,4-Dichlorophenyl | " | " | " | 2 | 20 | 100 | 10.0 |
| 4A | 2,4-Dichlorophenyl | Methyl | H | Methyl | 0 | 20 | 100 | 10.0 |
| 5Aa | 2,4-Dichlorophenyl | " | " | " | 1 | 1 | 100 | 10.0 |
|  |  |  |  |  |  | 20 | 100 | 10.0 |
| 5Ab | 2,4-Dichlorophenyl | " | " | " | 1 | 20 | 100 | 10.0 |
| 6A | 2,4-Dichlorophenyl | " | " | " | 2 | 1 | 100 | 10.0 |
|  |  |  |  |  |  | 20 | 100 | 10.0 |
| 7A | 2,4-Dichlorophenyl | Methyl | H | n-Pentyl | 0 | 20 | 100 | 9.5 |
| 8Aa | 2,4-Dichlorophenyl | " | " | " | 1 | 1 | 70 | 5.1 |
|  |  |  |  |  |  | 20 | 100 | 10.0 |
| 8Ab | 2,4-Dichlorophenyl | " | " | " | 1 | 20 | 100 | 10.0 |
| 9A | 2,4-Dichlorophenyl | " | " | " | 2 | 20 | 100 | 10.0 |
| 10A | 2,4-Dichlorophenyl | Methyl | H | Ethyl | 0 | 1 | 100 | 9.6 |
| 11Aa | 2,4-Dichlorophenyl | " | " | " | 1 | 1 | 100 | 10.0 |
| 11Ab | 2,4-Dichlorophenyl | " | " | " | 1 | 1 | 100 | 10.0 |
| 12A | 2,4-Dichlorophenyl | " | " | " | 2 | 1 | 100 | 10.0 |
| 13A | 2,4-Dichlorophenyl | Methyl | H | Isopropyl | 0 | 1 | 50 | 5.8 |
| 14Aa | 2,4-Dichlorophenyl | " | " | Isopropyl | 1 | 1 | 50 | 4.7 |
| 14Ab | 2,4-Dichlorophenyl | " | " | Isopropyl | 1 | 1 | 60 | 6.1 |
| 15A | 2,4-Dichlorophenyl | " | " | Isopropyl | 2 | 1 | 60 | 6.7 |
| 16A | 2,4-Difluorophenyl | Methyl | H | Methyl | 0 | 1 | 100 | 9.7 |
| 17Aa | 2,4-Difluorophenyl | " | " | " | 1 | 1 | 100 | 10.0 |
| 18A | 2,4-Difluorophenyl | " | " | " | 2 | 1 | 100 | 10.0 |
| 21A | 2,4-Difluorophenyl | Methyl | H | Ethyl | 2 | 1 | 90 | 8.9 |
| 23A | p-Fluorophenyl | Methyl | H | Methyl | 2 | 1 | 20 | 2.8 |
| 25A | Phenyl | Methyl | H | Methyl | 2 | 1 | 10 | 1.6 |
| 27A | 2,4-Dichlorophenyl | Ethyl | H | Methyl | 1 | 1 | 100 | 9.6 |
| 27Ab | 2,4-Dichlorophenyl | " | " | " | 1 | 1 | 100 | 8.3 |
| 28A | 2,4-Dichlorophenyl | " | " | " | 2 | 1 | 50 | 5.2 |
| 30a | 2,4-Dichlorophenyl | Methyl | Methyl | Methyl | 1 | 1 | 100 | 10.0 |
| 30b | 2,4-Dichlorophenyl | " | " | " | 1 | 1 | 100 | 10.0 |
| 31 | 2,4-Dichloro- | " | " | " | 2 | 1 | 100 | 10.0 |

TABLE 1-continued

Antifungal activity in vivo $$\begin{array}{c} \text{N}\!\!=\!\!\text{N} \\ \text{N}\!\!-\!\!\text{N} \\ | \\ \text{CH}_2\!\!-\!\!\underset{|}{\overset{|}{\text{C}}}\!\!-\!\!\underset{|}{\overset{\text{OH}}{\overset{|}{\text{C}}}}\!\!-\!\!\text{S}\!\!-\!\!\overset{(\text{O})_n}{\overset{\uparrow}{\text{R}^3}} \\ \text{Ph} \quad \text{R}^2 \end{array} \quad (I)$$

| Compound No. | Ph | $R^1$ | $R^2$ | $R^3$ | n | Dose (mg/kg) (p.o.) | Survival rate at complete death of non-medicated group (%) | Average survival days(s) |
|---|---|---|---|---|---|---|---|---|
| 33a | 2,4-Dichloro-phenyl | Methyl | Methyl | n-Propyl | 1 | 1 | 70 | 6.9 |
| 33b | 2,4-Dichloro-phenyl | " | " | " | 1 | 1 | 70 | 6.2 |
| 34 | 2,4-Dichloro-phenyl | " | " | " | 2 | 1 | 70 | 7.3 |
| 36a | 2,4-Dichloro-phenyl | Methyl | Methyl | n-Pentyl | 1 | 1 | 70 | 5.2 |
| 36b | 2,4-Dichloro-phenyl | " | " | " | 1 | 1 | 40 | 4.0 |
| 37 | 2,4-Dichloro-phenyl | " | " | " | 2 | 1 | 30 | 4.0 |
| Control | | | | | | 0 | 0 | 1.2 |

As can be seen from the above results, the N-substituted triazole derivatives (I) show an excellent antifungal activity. Advantageously, the N-substituted triazole derivatives (I) are quite low in toxicity, and their $LD_{50}$ values are more than 500 mg/kg when determined by oral route to mice. Thus, they are useful as antifungal agents.

The N-substituted triazole derivatives (I) and their physiologically accetable acid addition salts can be administered as such or in a conventional pharmaceutical preparation form together with any excipient or additive such as a carrier, a diluent or a dispersant orally or parenterally. For instance, they can be administered in the form of conventional solid or liquid pharmaceutical preparations such as solutions, suspensions, powders, granules capsules, tablets, injections, ointments, tinctures, etc. These preparations may be formulated in per se conventional procedures. The daily dosage may vary depending upon the state of infection, the age and body weight of patients, the administration route, etc., and the normal oral dosage to a human adult is between 10 and 3,000 mg, preferably between 10 and 200 mg, dividing in one to several times per day.

Practical and presently preferred embodiments of the invention are illustratively shown in the following examples, which are not intended to limit the scope of the invention thereto.

EXAMPLE 1

To a suspension of 50 % sodium hydride (3.46 g; 86.5 mmol) in dimethylsulfoxide (40 ml) was added trimethylsulfoxonium iodide (19.05 g; 86.6 mmol) at 0 to 10° C. To the resulting solution was added dropwise 2',4'-dichloro-2-n-propylthiopropiophenone (8.0 g; 28.9 mmol) in dimethylsulfoxide (35 ml) at 50 to 60° C., and the mixture was kept at 55 to 65° C. for 6 hours. After cooling, the reaction mixture was poured into ice water (700 ml) and the aqueous mixture was extracted with ether. The ether extract was washed with water, dried over magnesium sulfate and concentrated in vacuo to give 2-(2,4-dichlorophenyl)-2-(2-n-propylthio)ethyloxirane (9.2 g) as an oil. This oil was used for the next step without further purification.

To a suspension of 50 % sodium hydride (3.46 g; 86.5 mmol) in dimethylformamide (90 ml) was added 1,2,4-triazole (5.98 g; 86.5 mmol) at 0 to 10° C. After the mixture was stirred at room temperature for 30 minutes, 2-(2,4-dichlorophenyl)-2-(2-n-propylthio)ethyloxirane (9.2 g) as obtained above was added and stirring at 100° C. was continued for 5 hours. The mixture was cooled and diluted with ice water (500 ml). The aqueous mixture was extracted with ether and the organic extract was washed with water, dried over magnesium sulfate and evaporated in vacuo to give a crude mixture of diastereomers of 2-(2,4-dichlorophenyl)-3-n-propylthio-1-(1,2,4-triazol-1-yl)butan -2-ol (10.8 g) as an oil. The oily mixture was chromatographed on silica gel (500 g), eluting with chloroform. The less polar diastereomer A (Compound 1A, 633 mg) was obtained from the first fraction as crystals. Yield, 6.1 %. m.p., 101.0– 103.5° C.

NMR (CDCl$_3$) $\delta$: 7.75 (1H, s), 7.83 (1H, s), 7.07–7.52 (3H, m), 5.05 and 5.43 (each 1H, d, J=14 Hz), 4.80 (1H,d, J=1 Hz), 3.79 (1H, q, J=7 Hz), 2.66–2.74 (2H, m), 1.63–1.74 (2H, m), 1.09 (3H, d, J=7 Hz), 1.06 (3H, t, J=7 Hz).

Anal Calcd. for C$_{15}$H$_{19}$Cl$_2$N$_3$OS: C, 49.99 %; H, 5.32 %; N, 11.66 %. Found: C, 50.28 %; H, 5.45 %; N, 11.46 %.

The more polar diastereomer B (Compound 1B, 442 mg) was obtained from the second fraction as crystals. Yield, 4.3 %. m.p., 92–96° C.

NMR (CDCl$_3$) $\delta$: 7.68 (1H, s), 7.95 (1H, s), 7.03–7.52 (3H, m), 4.49 and 5.38 (each 1H, d, J=14 Hz), 4.47 (1H, s), 4.06 (1H, q, J=7 Hz), 1.90–2.16 (2H, m), 1.56 (3H, d, J=7 Hz), 1.36 (2H, sextet, J=7 Hz), 0.78 (3H, t, J=7 Hz).

Anal Calcd. for C$_{15}$H$_{19}$Cl$_2$N$_3$OS.½H$_2$O: C, 48.78 %; H, 5.46 %; N, 11.38 %. Found: C, 48.75 %; H, 5.46 %; N, 11.52 %.

EXAMPLE 2A

To a solution of 2-(2,4-dichlorophenyl)-3-n-propylthio-1-(1,2,4-triazol-1-yl)butan-2-ol (Compound 1A, m.p., 101.0–103.5° C.) (510 mg; 1.42 mmol) in chloroform (4 ml) was added m-chloroperbenzoic acid (244 mg; 1.42 mmol), and the resulting mixture was stirred at 0 to 10° C. for 1.5 hours. The reaction mixture was washed with aqueous ammonia and water, dried over magnesium sulfate and evaporated in vacuo to give a crude mixture of diastereomers of 2-(2,4-dichlorophenyl)-3-n-propylsulfinyl-1-(1,2,4-triazol-1-yl)butan-2-ol as an oil. The oily mixture was chromatographed on silica gel (60 g), eluting with chloroform-methanol (100 : 1). The less polar diastereomer a (Compound 2Aa, 140 mg) was obtained from the first fraction as crystals. Yield, 26.3 %. m.p., 135.0–136.0° C.

NMR (CDCl$_3$) δ: 7.73 (1H, s), 7.78 (1H, s), 7.00–7.48 (3H, m), 5.57 (1H, s), 5.23 and 5.53 (each 1H, d, J=14 Hz), 3.90 (1H, m), 2.6–3.0 (2H, m), 1.93 (2H, sextet, J=7.5 Hz), 1.13 (3H, t, J=7.5 Hz), 0.93 (3H, d, J=7.5 Hz).

Anal Calcd. for C$_{15}$H$_{19}$Cl$_2$N$_3$O$_2$S: C, 47.87 %; H, 5.09 %; N, 11.17 %. Found: C, 47.98 %; H, 5.26 %; N, 11.07 %.

The more polar diastereomer b (Compound 2Ab, 300 mg) was obtained from the second fraction as crystals. Yield, 56.6 %. m.p., 156.0–157.5° C.

NMR (CDCl$_3$) δ: 8.07 (1H, s), 7.68 (1H, s), 7.07–7.57 (3H, m), 5.52 (1H, s), 5.00 and 5.33 (each 1H, d, J=14 Hz), 3.83 (1H, q, J=7.5 Hz), 2.43–3.10 (2H, m), 1.53–2.07 (2H, m), 1.15 (6H, t, J=7.5 Hz).

Anal Calcd. for C$_{15}$H$_{19}$Cl$_2$N$_3$O$_2$S: C, 47.87 %; H, 5.09 %; N, 11.17 %. Found: C, 47.75 %; H, 5.18 %; N, 10.94 %.

EXAMPLE 2B

The reaction was carried out in the same manner as in Example 2A but using Compound 1B (m.p., 92–96° C.) in place of Compound 1A (m.p., 101.0–103.5° C.) to give two diastereomers of 2-(2,4-dichlorophenyl)-3-n-propylsulfinyl-1-(1,2,4-triazol-1-yl)butan-2-ol (Compounds 2Ba and 2Bb).

Compound 2Ba
m.p., 144–148° C.

NMR (CDCl$_3$) δ: 7.89 (1H, s), 7.75 (1H, s), 7.09–7.42 (3H, m), 5.71 (1H, d, J=2 Hz), 4.54 and 5.41 (each 1H, d, J=14 Hz), 4.06 (1H, m), 2.43–2.76 (2H, m), 1.68 (3H, d, J=7 Hz), 0.95 (3H, t, J=7 Hz).

Anal Calcd. for C$_{15}$H$_{19}$C;$_2$N$_3$O$_2$S: C, 47.87 %; H, 5.09 %; N, 11.17 %. Found: C, 48.02 %; H, 5.29 %; N, 10.97 %.

Compound 2Bb
m.p., 150–151.0° C.

NMR (CDCl$_3$) δ: 7.99 (1H, s), 7.67 (1H, s), 7.15–7.59 (3H, m), 4.61 and 5.17 (each 1H, d, J=14 Hz), 5.16 (1H, m), 3.93 (1H, q, J=7 Hz), 2.37–2.78 (2H, m), 1.5–1.8 (2H, m), 1.59 (3H, d, J=7 Hz), 0.99 (3H, t, J=7 Hz).

Anal Calcd. for C$_{15}$H$_{19}$C;$_2$N$_3$O$_2$S: C, 47.87 %; H, 5.09 %; N, 11.17 %. Found: C, 47.59 %; H, 5.18 %; N, 11.09 %.

EXAMPLE 3A

To a solution of 2-(2,4-dichlorophenyl)-3-n-propylthio-1-(1,2,4-triazol-1-yl)butan-2-ol (Compound 1A, m.p., 101.0–103.5° C.) (358 mg; 0.99 mmol) in chloroform (10 ml) was added m-chloroperbenzoic acid (515 mg; 2.97 mmol) at room temperature, and the resulting mixture was stirred at 0 to 10° C. for 2 hours. The reaction mixture was washed with aqueous ammonia and water, dried over magnesium sulfate and evaporated in vacuo. The oily residue was chromatographed on silica gel (35 g), eluting with chloroform, to give 2-(2,4-dichlorophenyl)-3-n-propylsulfonyl-1-(1,2,4-triazol-1-yl)butan-2-ol (Compound 3A, 150 mg) as crystals. Yield, 38.5 %. m.p., 150–156° C.

NMR (CDCl$_3$) δ: 7.75 (1H, s), 7.80 (1H, s), 7.09–7.44 (3H, m), 5.61 (1H, s), 5.36 and 5.59 (each 1H, d, J=14 Hz), 4.13 (1H, m), 3.11–3.43 (2H, m), 1.9–2.1 (2H, m), 1.20 (3H, d, J=7 Hz), 1.15 (3H, t, J=7 Hz).

Anal Calcd. for C$_{15}$H$_{19}$Cl$_2$N$_3$O$_3$S: C, 45.92 %; H, 4.88 %; H, 10.71 %. Found: C, 45.86 %; H, 5.03 %; N, 10.50 %.

EXAMPLE 3B

The reaction was carried out in the same manner as in Example 3A but using Compound 1B (m.p., 92–96° C.) in place of Compound 1A (m.p., 101.0–103.5° C.) to give 2-(2,4-dichlorophenyl)-3-n-propylsulfonyl-1-(1,2,4-triazol-1-yl)-butan-2-ol (Compound 3B) as an oil.

NMR (CDCl$_3$) δ: 7.63 (1H, s), 7.93 (1H, s), 7.03–7.45 (3H, m), 5.50 (1H, s), 4.53 and 5.27 (each 1H, d, J=14 Hz), 4.40 (1H, q, J=7.5 Hz), 2.4–2.8 (2H, m), 1.5–1.9 (2H, m), 1.73 (3H, d, J=7.5 Hz), 0.90 (3H, t, J=7.5 Hz).

Anal Calcd. for C$_{15}$H$_{19}$Cl$_2$N$_3$O$_3$S.H$_2$O: C, 43.87 %; H, 5.12 %; N, 10.24 %. Found: C, 43.51 %; H, 5.01 %; N, 9.95 %.

EXAMPLES 4 to 28

In the same manner as in Example 1, 2A, 2B, 3A or 3B, the N-substituted triazole derivatives (I) as shown in Table 2 were produced.

TABLE 2

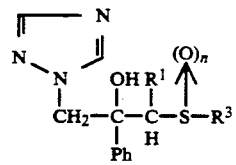

| Example No. | Compound No. | Ph | R$^1$ | R$^3$ | n | m.p. (°C.) |
|---|---|---|---|---|---|---|
| 4 | 4A | 2,4-Dichlorophenyl | Methyl | Methyl | 0 | 122–123 |
|  | 4B | " | " | " | 0 | 101–105 |
| 5A | 5Aa | " | " | " | 1 | 200–202 |
|  | 5Ab | " | " | " | 1 | 211–212 |
| 5B | 5Ba | " | " | " | 1 | 167–168 |
|  | 5Bb | " | " | " | 1 | 206–208 |

TABLE 2-continued

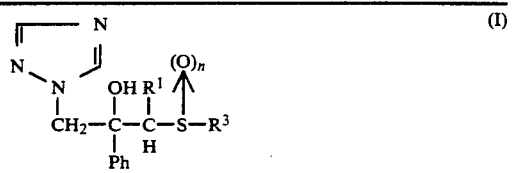

(I)

| Example No. | Compound No. | Ph | R¹ | R³ | n | m.p. (°C.) |
|---|---|---|---|---|---|---|
| 6A | 6A | " | " | " | 2 | 182–183 |
| 6B | 6B | " | " | " | 2 | 183–186 |
| 7 | 7A | " | " | n-Pentyl | 0 | 74–75 |
|  | 7B | " | " | " | 0 | 87–90 |
| 8A | 8Aa | " | " | " | 1 | 120–122 |
|  | 8Ab | " | " | " | 1 | 168–170 |
| 8B | 8Ba | " | " | " | 1 | 138–140 |
|  | 8Bb | " | " | " | 1 | 167–169 |
| 9A | 9A | " | " | " | 2 | 110–112 |
| 9B | 9B | " | " | " | 2 | 113–114 |
| 10 | 10A | " | " | Ethyl | 0 | 118–119.5 |
|  | 10B | " | " | " | 0 | 103.5–106 |
| 11A | 11Aa | 2,4-Dichlorophenyl | Methyl | Ethyl | 1 | 155–156 |
|  | 11Ab | " | " | " | 1 | 160–161 |
| 12A | 12A | " | " | " | 2 | 154–155 |
| 13 | 13A | " | " | Isopropyl | 0 | 97–98 |
|  | 13B | " | " | " | 0 | 110–111.5 |
| 14A | 14Aa | " | " | " | 1 | 124–125 |
|  | 14Ab | " | " | " | 1 | 181–182 |
| 15A | 15A | " | " | " | 2 | 177–178 |
| 16 | 16A | 2,4-Difluorophenyl | " | Methyl | 0 | 122–123 |
|  | 16B | " | " | " | 0 | 106–108.5 |
| 17A | 17Aa | " | " | " | 1 | 158–161 |
| 18A | 18A | " | " | " | 2 | 211–212 |
| 19 | 19A | " | " | Ethyl | 0 | 96–97 |
|  | 19B | " | " | " | 0 | 76–77.5 |
| 20A | 20Aa | " | " | " | 1 | 127–128 |
|  | 20Ab | " | " | " | 1 | 181.5–183 |
| 21A | 21A | " | " | " | 2 | 147–149 |
| 22 | 22A | p-Fluorophenyl | " | Methyl | 0 | 122–123 |
|  | 22B | " | " | " | 0 | 92–95 |
| 23A | 23A | " | " | " | 2 | 174–175 |
| 23B | 23B | " | " | " | 2 | 154–155 |
| 24 | 24A | Phenyl | Methyl | Methyl | 0 | 89–90 |
|  | 24B | " | " | " | 0 | 57–60 |
| 25A | 25A | " | " | " | 2 | 152–153 |
|  | 25B | " | " | " | 2 | 169–171 |
| 26 | 26A | 2,4-Dichlorophenyl | Ethyl | " | 0 | oil |
|  | 26B | " | " | " | 0 | oil |
| 27A | 27Aa | " | " | " | 1 | 175–176 |
|  | 27Ab | " | " | " | 1 | 185–186 |
| 28A | 28A | " | " | " | 2 | 177–178 |
| 28B | 28B | " | " | " | 2 | 93–96 |

EXAMPLE 29

To a solution of trimethylsulfonium methylsulfate (11.54 g; 61.4 mmol) in acetonitrile (60 ml) was added 2',4'-dichloro-alpha-methylthioisobutylophenone (8.0 g; 30.4 mmol) and sodium methoxide (3.62 g; 67 mmol) at room temperature, and the mixture was stirred at room temperature for 2 hours. The solvent was removed in vacuo and the residue was extracted with ethyl acetate. The extract was washed with water, dried over magnesium sulfate and evaporated to give 2-(2,4-dichlorophenyl)-2-(2-methylthioprop-2-yl)oxirane (7.0 g) as an oil. This oil was used for the subsequent reaction without further purification.

To a suspension of 60 % sodium hydride (3.5 g; 87.5 mmol) in dimethylformamide (70 ml) was added 1,2,4-triazole (7.0 g; 101 mmol) at room temperature. After the mixture was stirred for 1 hour, 2-(2,4-dichlorophenyl)-2-methylthioprop-2-yl)oxirane (7.0 g) was added and stirring was continued at 100° C. for 7 hours. The mixture was cooled and diluted with ice water. The aqueous mixture was extracted with toluene and the organic extract was washed with water, dried over magnesium sulfate and evaporated in vacuo. The oily residue was chromatographed on silica gel, eluting with chloroform, to give 2-(2,4-dichlorophenyl)-3-methyl-3-methylthio-1-(1,2,4-triazol-1-yl)butan-2-ol (1.25 g). Yield, 14.3 %. m.p., 80–83° C.

NMR (CDCl$_3$) δ: 1.35 (3H, s), 1.43 (3H, s), 2.10 (3H, s), 4.95 and 5.90 (each 1H, d, J=14 Hz), 5.78 (1H, s), 7.10–7.50 (3H, m), 7.90 (1H, s), 8.25 (1H, s).

Anal Calcd. for $C_{14}H_{17}Cl_2N_3OS$: C, 48.55 %; H, 4.91 %; N, 12.14 %. Found: C, 48.38 %; H, 4.99 %; N, 11.95 %.

EXAMPLE 30

To an ice-cold solution of 2-(2,4-dichlorophenyl)-3-methyl-3-methylthio-1-(1,2,4-triazol-1-yl)butan-2-ol (1.25 g) in chloroform (50 ml) was added m-chloroperbenzoic acid (199 mg), and the mixture was allowed to stand at 0 to 10° C. for 1 hour. The reaction mixture was washed with aqueous ammonia and water, dried over magnesium sulfate and evaporated in vacuo to give a crude mixture of diastereomers of 2-(2,4-dichlorophenyl)-3-methyl-3-methylsulfinyl-1-(1,2,4-triazol-1-yl)butan-2-ol as an oil. The oily mixture was chromatographed on silica gel, eluting with chloroform. The less polar diastereomer a (Compound 30a, 42 mg) was obtained from the first fraction as crystals. Yield, 3.2 %. m.p., 165–166° C.

NMR (CDCl$_3$) δ: 1.30 (3H, s), 1.45 (3H, s), 2.63 (3H, s), 4.71 and 6.12 (each 1H, d, J=14 Hz), 6.28 (1H, s), 7.1–7.25 (2H, m), 7.75 (1H, s), 7.85 (1H, d, J=7 Hz), 8.26 (1H, s).

Anal Calcd. for $C_{14}H_{17}Cl_2N_3O_2S$: C, 46.41 %; H, 4.69 %; N, 11.60 %. Found: C, 46.35 %; H, 4.77 %; N, 11.41 %.

The more polar diastereomer b (Compound 30b, 87 mg) was obtained from the second fraction as crystals. Yield, 6.7 %. m.p., 166–167° C.

NMR (CDCl$_3$) δ: 1.02 (3H, s), 1.51 (3H, s), 2.69 (3H, s), 4.88 and 5.98 (each 1H, d, J=14 Hz), 6.32 (1H, s), 7.1–7.25 (2H, m), 7.70 (1H, s), 7.85 (1H, d, J=7 Hz), 8.27 (1H, s).

Anal Calcd. for $C_{14}H_{17}Cl_2N_3O_2S$: C, 46.41 %; H, 4.69 %; N, 11.60 %. Found: C, 46.29 %; H, 4.85 %; N, 11.47 %.

EXAMPLE 31

To an ice-cold solution of 2-(2,4-dichlorophenyl)-3-methyl-3-methylsulfinyl-1-(1,2,4-triazol-1-yl)butan-2-ol (Compound 30b, 346 mg) in chloroform (50 ml) was added m-chloroperbenzoic acid (350 mg), and the mixture was stirred at 0 to 10° C. for 1 hour. The reaction mixture was washed with aqueous ammonia and water, dried over magnesium sulfate and evaporated in vacuo. The oily residue was chromatographed on silica gel, eluting with chloroform, to give 2-(2,4-dichlorophenyl)-3-methyl-3-methylsulfonyl-1-(1,2,4-triazol-1-yl)butan-2-ol (120 mg) as crystals. Yield, 31.7 m.p., 209–210° C.

NMR (CDCl$_3$) δ: 1.30 (3H, s), 1.62 (3H, s), 3.22 (3H, s), 5.32 and 5.98 (each 1H, d, J=14 Hz), 6.58 (1H, s), 7.15–7.30 (2H, m), 7.72 (1H, s), 8.25 (1H, s), 7.90 (1H, d, J=6 Hz).

EXAMPLES 32 to 37

In the same manner as in Example 29, 30 or 31, the N-substituted triazole derivatives (I) as shown in Table 3 were produced.

TABLE 3

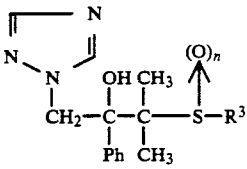

| Example No. | Compound No. | Ph | R$^3$ | n | m.p. (°C.) |
|---|---|---|---|---|---|
| 32 | 32 | 2,4-Dichlorophenyl | n-Propyl | 0 | oil |
| 33 | 33a | 2,4-Dichlorophenyl | " | 1 | 120–121 |
|  | 33b | 2,4-Dichlorophenyl | " | 1 | 136–137 |
| 34 | 34 | 2,4-Dichlorophenyl | " | 2 | 146–148 |
| 35 | 35 | 2,4-Dichlorophenyl | n-Pentyl | 0 | oil |
| 36 | 36a | 2,4-Dichlorophenyl | " | 1 | 78–80 |
|  | 36b | 2,4-Dichlorophenyl | " | 1 | 103–105 |
| 37 | 37 | 2,4-Dichlorophenyl | " | 2 | 147–148 |

EXAMPLE 38

To a solution of 2-(2,4-dichlorophenyl)-3-mesyloxy-1-(triazol-1-yl)butan-2-ol (100 mg; 0.263 mmol) in dimethylsulfoxide (1 ml) was added 15 % aqueous methanethiol sodium salt at room temperature, and the mixture was stirred at 50 to 60° C. for 8 hours. The reaction mixture was diluted with water and extracted with ether. The extract was washed with water, dried over magnesium sulfate and evaporated in vacuo to give 2-(2,4-dichlorophenyl)-3-methylthio-1-(triazol-1-yl)butan-2-ol (71 mg, 81 %) as crystals. m.p., 122–123° C. This compound was identical with Compound 4A obtained in Example 4.

REFERENCE EXAMPLE 1

To a suspension of 60 % sodium hydride (5.62 g; 0.141 mol) in dimethylsulfoxide (100 ml) was added trimethyloxosulfonium iodide (30.8 g; 0.14 mol) at room temperature, and stirring was continued at the same temperature for 1 hour. To the mixture was added a solution of 2',4'-dichloro-2-tetrahydropyranyloxypropiophenone (14.15 g; 0.0467 mol) in dimethylsulfoxide (20 ml) at room temperature, and the mixture was stirred at the same temperature for 12 hours. The reaction mixture was poured into ice water, and the aqueous mixture was extracted with toluene. The organic layer was washed with water, dried over magnesium sulfate and evaporated in vacuo to give 2-(2,4-dichlorophenyl)-2-(2-tetrahydropyranyloxy)ethyloxirane (13.68 g, 92 %) as an oil.

REFERENCE EXAMPLE 2

To a suspension of 60 % sodium hydride (5.18 g; 0.129 mol) in dimethylformamide (70 ml) was added a solution of 1,2,4-triazole (8.94 g; 0.129 mol) in dimethylformamide (20 ml) at room temperature, and the mixture was stirred at the same temperature for 1 hour. To the resulting solution was added 2-(2,4-dichlorophenyl)-2-(2-tetrahydropyranyloxy)ethyloxirane (13.68 g; 0.043 mol) obtained in Reference Example 1 at room temperature, and stirring was continued at 80 to 90° C. for 3 hours. After cooling, the reaction mixture was concentrated in vacuo. The oily residue was quenched with water and extracted with toluene. The organic layer was washed with water, dried over magnesium sulfate and concentrated in vacuo to give 2-(2,4-dichlorophenyl)-3-tetrahydropyranyloxy-1-(1,2,4-triazol-1-yl)butan-2-ol (14.89 g, 89 %) as an oil.

REFERENCE EXAMPLE 3

A mixture of 2-(2,4-dichlorophenyl)-3-tetrahydropyranyloxy-1-(1,2,4-triazol-1-yl)butan-2-ol (14.59 g, 0.0378 mol) obtained in Reference Example 2 and 10 % hydrochloric acid (52.5 ml) was stirred at room temperature for 3 hours, and the reaction mixture was neutralized with 20 % aqueous sodium hydroxide. The resulting precipitate was collected by filtration, washed with ether and dried to give 2-(2,4-dichlorophenyl)-3-hydroxy-1-(1,2,4-triazol-1-yl)butan-2-ol (7.95 g, 70 %) as crystals. m.p., 204–206° C.

REFERENCE EXAMPLE 4

To a suspension of 2-(2,4-dichlorophenyl)-3-hydroxy-1-(triazol-1-yl)butan-2-ol (1.0 g; 3.3 mmol) obtained in Reference Example 3 in benzene (10 ml) was added triethylamine (1.0 g; 9.9 mmol) and methanesulfonyl chloride (0.76 g; 6.6 mmol) at 25 to 40° C., and the mixture was stirred at room temperature for 1 hour. The reaction mixture was poured into ice water and extracted with ethyl acetate. The organic layer was washed with aqueous sodium hydrogen bicarbonate and water, dried over magnesium sulfate and evaporated in vacuo to give 2-(2,4-dichlorophenyl)-3-mesyloxy-1-(triazol-1-yl)butan-2-ol (1.26 g, 100 %) as crystals m.p., 147–149° C.

What is claimed is:

1. An N-substituted triazole compound of the formula

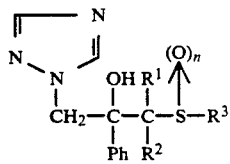

wherein Ph is a 2,4-dichlorophenyl or 2,4-difluorophenyl group, $R^1$ and $R^3$ are each methyl, $R^2$ is a hydrogen atom or a $C_1$–$C_3$ alkyl group, and n is 1 or 2, or an acid addition salt thereof, said compound being in a racemic, diastereomer or optically active form thereof.

2. The compound according to claim 1, wherein Ph is a 2,4-dichlorophenyl group, $R^2$ is a hydrogen atom $R^1$ and $R^3$ are each a methyl group and n is 1.

3. The compound according to claim 1, wherein Ph is a 2,4-dichlorophenyl group, $R^2$ is a hydrogen atom $R^1$ and $R^3$ are each a methyl group and n is 2.

4. The compound according to claim 1, wherein Ph is a 2,4-difluorophenyl group, $R^1$ and $R^3$ are each a methyl group and n is 1.

5. The compound according to claim 1, herein Ph is a 2,4-difluorophenyl group, $R^1$ and $R^3$ are each a methyl group and n is 2.

6. The compound according to claim 1, wherein Ph is a 2,4-dichlorophenyl group, $R^2$ is $C_1$–$C_4$ alkyl group $R^1$ and $R^3$ are each a methyl group and n is 1.

7. The compound according to claim 1, wherein Ph is a 2,4-dichlorophenyl group, $R^2$ is a $C_1$–$C_4$ alkyl group, $R^1$ and $R^3$ are each a methyl group and n is 2.

8. The compound according to claim 2, which is in a racemic form.

9. The compound according to claim 3, which is in a racemic form.

10. The compound according to claim 4, which is in a racemic form.

11. The compound according to claim 5, which is in a racemic form.

12. The compound according to claim 6, which is in a racemic form.

13. The compound according to claim 7, which is in a racemic form.

14. The compound according to claim 2, which is in a diastereomer form.

15. The compound according to claim 3, which is in a diastereomer form.

16. The compound according to claim 4, which is in a diastereomer form.

17. The compound according to claim 5, which is in a diastereomer form.

18. The compound according to claim 6, which is in a diastereomer form.

19. The compound according to claim 7, which is in a diastereomer form.

20. The compound according to claim 2, which is in a optically active form.

21. The compound according to claim 3, which is in a optically active form.

22. The compound according to claim 4, which is in a optically active form.

23. The compound according to claim 5, which is in a optically active form.

24. The compound according to claim 6, which is in a optically active form.

25. The compound according to claim 7, which is in a optically active form.

26. An antifungal composition which comprises as an active ingredient an antifungally effective amount of the N-substituted triazole compound according to claim 2, or an acid addition salt thereof, and a pharmaceutically acceptable carrier or diluent.

27. An antifungal composition which comprises as an active ingredient an antifungally effective amount of the N-substituted triazole compound according to claim 3, or an acid addition salt thereof, and a pharmaceutically acceptable carrier or diluent.

28. An antifungal composition which comprises as an active ingredient an antifungally effective amount of the N-substituted triazole compound according to claim 4, or an acid addition salt thereof, and a pharmaceutically acceptable carrier or diluent.

29. An antifungal composition which comprises as an active ingredient an antifungally effective amount of the N-substituted triazole compound according to claim 5, or an acid addition salt thereof, and a pharmaceutically acceptable carrier or diluent.

30. An antifungal composition which comprises as an active ingredient an antifungally effective amount of the N-substituted triazole compound according to claim 6, or an acid addition salt thereof, and a pharmaceutically acceptable carrier or diluent.

31. An antifungal composition which comprises as an active ingredient an antifungally effective amount of the N-substituted triazole compound according to claim 7, or an acid addition salt thereof, and a pharmaceutically acceptable carrier or diluent.

32. An antifungal composition which comprises as an active ingredient an antifungally effective amount of the N-substituted triazole compound according to claim 20, or an acid addition salt thereof, and a pharmaceutically acceptable carrier or diluent.

33. An antifungal composition which comprises as an active ingredient an antifungally effective amount of the N-substituted triazole compound according to claim 21, or an acid addition salt thereof, and a pharmaceutically acceptable carrier or diluent.

34. An antifungal composition which comprises as an active ingredient an antifungally effective amount of the N-substituted triazole compound according to claim 22, or an acid addition salt thereof, and a pharmaceutically acceptable carrier or diluent.

35. An antifungal composition which comprises as an active ingredient an antifungally effective amount of the N-substituted triazole compound according to claim 23, or an acid addition salt thereof, and a pharmaceutically acceptable carrier or diluent.

36. An antifungal composition which comprises as an active ingredient an antifungally effective amount of the N-substituted triazole compound according to claim 24, or an acid addition salt thereof, and a pharmaceutically acceptable carrier or diluent.

37. An antifungal composition which comprises as an active ingredient an antifungally effective amount of the N-substituted triazole compound according to claim 25, or an acid addition salt thereof, and a pharmaceutically acceptable carrier or diluent.

38. A method for treating fungal infections which comprises administering to a patient an antifungally effective amount of a compound according to claim 2, or a pharmaceutically acceptable salt thereof.

39. A method for treating fungal infections which comprises administering to a patient an antifungally effective amount of a compound according to claim 3, or a pharmaceutically acceptable salt thereof.

40. A method for treating fungal infections which comprises administering to a patient an antifungally effective amount of a compound according to claim 4, or a pharmaceutically acceptable salt thereof.

41. A method for treating fungal infections which comprises administering to a patient an antifungally effective amount of a compound according to claim 5, or a pharmaceutically acceptable salt thereof.

42. A method for treating fungal infections which comprises administering to a patient an antifungally effective amount of a compound according to claim 6, or a pharmaceutically acceptable salt thereof.

43. A method for treating fungal infections which comprises administering to a patient an antifungally effective amount of a compound according to claim 7, or a pharmaceutically acceptable salt thereof.

44. A method for treating fungal infections which comprises administering to a patient an antifungally effective amount of a compound according to claim 20, or a pharmaceutically acceptable salt thereof.

45. A method for treating fungal infections which comprises administering to a patient an antifungally effective amount of a compound according to claim 21, or a pharmaceutically acceptable salt thereof.

46. A method for treating fungal infections which comprises administering to a patient an antifungally effective amount of a compound according to claim 22, or a pharmaceutically acceptable salt thereof.

47. A method for treating fungal infections which comprises administering to a patient an antifungally effective amount of a compound according to claim 23, or a pharmaceutically acceptable salt thereof.

48. A method for treating fungal infections which comprises administering to a patient an antifungally effective amount of a compound according to claim 24, or a pharmaceutically acceptable salt thereof.

49. A method for treating fungal infections which comprises administering to a patient an antifungally effective amount of a compound according to claim 25 or a pharmaceutically acceptable salt thereof.

* * * * *